United States Patent [19]

Strobel

[11] 4,129,521

[45] * Dec. 12, 1978

[54] BRANCHED CHAIN NONYL AND DODECYL ISOMERIC MIXTURES OF 2-(5'-NONYL, OR DODECYL-2'-HYDROXYPHENYL)BENZO-TRIAZOLE AS UV STABILIZERS

[75] Inventor: Albert F. Strobel, Delmar, N.Y.

[73] Assignee: GAF Corporation, New York, N.Y.

[*] Notice: The portion of the term of this patent subsequent to Sep. 28, 1993, has been disclaimed.

[21] Appl. No.: 727,428

[22] Filed: Sep. 28, 1976

Related U.S. Application Data

[63] Continuation-in-part of Ser. No. 500,083, Aug. 23, 1974, Pat. No. 3,983,132.

[51] Int. Cl.$^2$ ............................................. C09K 15/22
[52] U.S. Cl. ................................. 252/403; 260/308 B
[58] Field of Search ............................... 252/403, 407; 260/308 B, 45.8 NT; 424/59, 174

[56] References Cited

U.S. PATENT DOCUMENTS

| 3,074,910 | 1/1963 | Dickson | 260/308 B |
| 3,230,194 | 1/1966 | Boyle | 260/308 B |

FOREIGN PATENT DOCUMENTS 7108447 12/1971 Netherlands ...................... 260/308 B

*Primary Examiner*—Benjamin R. Padgett
*Assistant Examiner*—Josephine L. Barr
*Attorney, Agent, or Firm*—Walter C. Kehm; Marilyn J. Maue

[57] ABSTRACT

This invention relates to a stabilization composition, particularly adapted to prevent deterioration resulting from exposure to heat and light in polymeric materials, paints and dyes consisting essentially of a normally liquid, branched chain nonyl, or dodecyl isomeric mixture of 2-(5'-nonyl, or -dodecyl-2'-hydroxy-phenyl) benzotriazole; to the method of preparing said stabilization composition and to the stabilized products having between about 0.05 and about 15 weight percent of said stabilization composition incorporated therein.

8 Claims, No Drawings

BRANCHED CHAIN NONYL AND DODECYL ISOMERIC MIXTURES OF 2-(5'-NONYL, OR DODECYL-2'-HYDROXYPHENYL)BENZOTRIAZOLE AS UV STABILIZERS

BACKGROUND OF THE INVENTION

This is a continuation-in-part of application Ser. No. 500,083 filed Aug. 23, 1974 now U.S. Pat. No. 3,983,132.

Olefinic polymers such as polyethylene, polypropylene, polyvinyl chloride, polystyrene and polyesters are subject to photo-oxidation when exposed to sunlight over extended periods of time. This photo-oxidation initiates deterioration of the polymer by breaking the polymer chain which results in formation of carbonyl groups in the molecule. Once begun the oxidation continues, the polyolefin cracks or crazes and loses tensile strength to the point of mechanical failure. A number of ultraviolet inhibitors have been proposed which inhibit photo-degradation of many polymers, resins and polyesters. However, some of the most effective of these known ultraviolet inhibitors, such as lower alkyl hydroxyphenyl benzotriazoles, are not compatible with such polyolefins as polyethylene, polypropylene and polystyrene and polymers which contain high molecular weight hydrocarbon chains due to exudation from the polymer soon after being incorporated therein.

Also it has been found that many effective stabilizers for halogen containing polymers such as polyvinyl chloride, polyvinylidene chloride and the like are often not effective stabilizers for hydrocarbon polyolefins. Stabilizers for halogen-containing polymers function essentially as halide scavengers, thus serving no purpose in the non-halogenated hydrocarbon olefinic polymers and which, in some cases, actually alter desirably properties of the hydrocarbon polymer. Similarly, certain stabilizers which are emminently suitable as UV inhibitors in such cellulose ester polymers as cellulose triacetate and cellulsoe acetate butyrate are not sufficiently effective for hydrocarbon polymers.

Although certain benzotriazole stabilizers have been recently proposed in U.S. Pat. Nos. 3,230,194 and 3,253,921, these benzotriazoles are normally solid substances which are mixed with the polymer to provide protection but which are not retained over long duration in the polymeric material and, therefore, do not provide lasting protection against UV light absorption. It is believed that these benzotriazoles in their normally solid state do not penetrate the internal polymeric structure for lasting incorporation therein. Similar difficulties are encountered with triazoles containing polar substituents such as $SO_2NH_2$, amine derivatives thereof, $SO_3Na$, $COONa$, etc. Additionally, in the case of the lower alkyl benzotriazoles, the lower alkyl substituents are known to be incompatible with high molecular weight hydrocarbon type polymers, as is the case with stabilizers proposed in U.S. Pat. No. 3,018,269. In other cases, crowding of the alkyl substituent adjacent to the -OH group on the phenol ring produced a hindered phenol moiety which alters the UV absorption range, so that compounds such as 2-(3'-alkyl-2'-hydroxyphenyl) benzotriazoles and the 2-hydroxyphenyl naphthotriazoles are not sufficiently sensitive to effectivley prevent deterioration due to UV light radiations within the critical 290 nm to 370 nm band range which most often causes the degradation of the polymer through discoloration and crazing.

In the case of non-polymeric materials, it is known that certain dyes are not resistant to the effects of sunlight and fade when exposed to UV radiation within the range of 250–400nm. Many transparent materials useful in sheets or films, in addition to developing undesirable color resulting in the reduction of transparency, also become brittle, lose their elasticity, crack and eventually completely deteriorate. Paints, varnishes, lacquers, and the like are particularly prone to these effects, and in connection with these latter materials, the transparency factor is of paramount concern. Thus, it is of prime importance that any stabilizer employed for these purposes by colorless and chemically inert so as to avoid coloration or formation of colored impurities.

It is therefore an object of this invention to provide an ultraviolet absorbent and heat stabilization material of the benzotriazole type capable of conferring a high degree of long lasting stability to the olefinic and other polymers and non-polymeric materials, which stabilizer is substantially colorless and which is obtained in a state capable of intimate and uniform penetration into the internal polymeric structure or molecular arrangement of non-polymeric materials.

Another object of this invention is to provide a stabilizer which displays optimum absorption activity for UV radiations within the range of 250 to 400 nm which functions as a complete sun-screen when employed in relatively high concentration.

It is another object of this invention to provide a method for preparing such an improved stabilizer of the benzotriazole type.

It is a further object of this invention to provide novel polymeric compositions containing a completely compatible stabilizer which provides sustained protection to the polymer and displays high tolerance for other additives in the polymeric formulation.

It is also an object of this invention to provide a stabilizers of the benzotriazole type which is highly soluble in a wide variety of solvents and which, therefore, is suitable for intimate incorporation in many substances including polymeric and non-polymeric materials.

It is still another object to provide a stabilizer of high efficiency and long duration for most polymeric materials, including halogen, oxygen and nitrogen containing polymers anf for paint dyes, varnishes and cosmetic substances.

Still another object is to obtain a stabilizing composition which is capable of providing sustained protection against deterioration by UV light radiation which is not readily exuded from a formulation or removed by mechanical abrasion.

These and other object of the present invention will become apparent from the following description and disclosure.

According to the present invention, a normally liquid composition for stabilizing heat and light sensitive materials, comprising essentially a normally liquid mixture of branched chain dodecyl isomers of 2-(5'-dodecyl-2'-hydroxyphenyl)benzotriazole is provided together with a method of preparing said liquid mixture and for preparing products, particularly plastic, paint or dye products, having incorporated therein between about 0.01% and about 15% by weight preferably between 0.05 and 10% by weight of said normally liquid mixture. Corresponding nonyl isomer compounds are also contemplated.

The 2-(5'-dodecyl-2'-hydroxyphenyl)benzotriazole isomeric mixtures which comprise the normally liquid stabilizers of the present invention consist essentially of secondary and tertiary dodecyl isomers substituted in the para position with respect to the hydroxy group of the phenol moiety. For the purposes of the present invention, the isomeric mixture generally contains at least 4 dodecyl isomers, preferably a mixture of 6 to 12 isomeric forms, wherein the predominant proportion of the dodecyl isomers contain a prependerance of carbon atoms in the alkyl carbon chain on which branching occurs, most preferably at least about 70% dodecyl isomers having at least 7 carbon atoms in an alkyl carbon chain. The n-dodecyl isomer is substantially eliminated from the present mixture by a selective manner in which the liquid mixture is prepared. However, when the present mixture of isomers is prepared by alternative methods, as in direct formulation of two or more certain selected branched chain types, trace amounts of the n-dodecyl isomer may be tolerated in the formulation. If desired, however, this isomer can be completely removed by extraction.

The dodecyl isomers are prepared from dodecene derived by the tetramerization of propylene. In like manner nonyl isomeric mixtures can be obtained from nonene derived by the trimerization of propylene.

The preferred method of preparing the normally liquid stabilizers comprising the 2-(5'-dodecyl-2'-hydroxyphenyl) benzotriazole isomeric mixtures involves coupling an o-nitrophenyl diazonium salt, obtained from the reaction of a 2-nitroaniline with an alkali metal nitrite in the presence of a mineral acid, with a mixture of branched chain dodecyl isomers of 4-dodecyl-phenol in the presence of a carboxylic acid, eg. glacial acetic acid or an alkali salt of the carboxylic acid, in an acid medium maintained at a pH of between about 3 and about 5.5, preferably at pH between 3.5 and 4.5.

The o-nitrophenyl diazonium salt employed in the coupling reaction is obtained by reacting 2-nitroaniline, eg. at a temperature between about $-7°$ C. and about $10°$ C. under substantially atomspheric pressure, with an equimolar amount or an excess of alkali metal nitrite in the presence of a strong non-oxidizing and non-reducing mineral acid such as a hydrogen halide, sulfuric acid, phosphoric acid, etc.; hydrochloric and sulfuric acids being preferred.

The nitroaniline reactant is dissolved in a suitable solvent. For example, a solution of the nitroaniline is formed by mixture with a carboxylic $C_2$ to $C_4$ acid, eg. glacial acetic acid, and the mineral acid is added to the solution to form a slurry. The resulting slurry of 2-nitroaniline is then reacted with the nitrite in the presence of a strong mineral acid referred to above. Suitable alkali metal nitrites include the nitrites of any of the alkaline or alkali earth metals and are preferably the sodium or potassium nitrites. Any excess nitrite which may remain after completion of the reaction can be neutralized with a suitable neutralizer eg. sulfamic acid.

In the present method of preparation, the above coupling reaction results in the formation of the branched chain 2-(2'-nitrophenylazo)-4-dodecyl phenols. The coupling reaction is effected in the presence of a $C_2$ to $C_5$ carboxylic acid or an alkali metal salt of a $C_2$ to $C_5$ carboxylic acid, preferably a sodium or potassium salt of acetic or propionic acid, at a temperature below $30°$ C., preferably between about $-15°$ C. and about $10°$ C. and advantageously under conditions of agitation for several hours, eg. 2 to 50 hours, to form the corresponding dodecyl isomeric mixture of 2-(2'-nitrophenylazo)-4-dodecyl-phenols obtained as an oily liquid phase over an aqueous phase containing water, acid and salts. The oily phase is separated by decantation or by any other convenient method, and can be temperature between $-15°$ C. and $75°$ C. at a pressure from 0 to 100 psig. for a period of from about 0.5 to about 2.5 hours preferably in the presence of a catalyst, eg. 0.5 to 2% of boron tri-fluoride catalyst, to provide a solution containing the corresponding branched chain mixture of 4-dodecyl-phenol isomers used in the present selective method of preparation. The product is essentially (more than 90%) p-dodecylphenol branched chain isomers. The 4-dodecyl isomers are recovered from the solution, eg. by washing with water to remove catalyst and distilling to remove any unreacted phenol.

It is also to be understood, however, that specific isomers include, for example, the 2,4,6,8-tetramethyloctyl isomer, may be selected and either added to the above isomeric mixture or may be independently combined to provide the present isomeric mixture of branched chain dodecyl isomers which are reacted with phenol as described above.

In the present method of preparation, the above coupling reaction results in the formation of the branched chain 2-(2'-nitrophenylazo)-4-dodecyl phenols. The coupling reaction is effected in the presence of a $C_2$ to $C_5$ carboxylic acid or an alkali metal salt of a $C_2$ to $C_5$ carboxylic acid, preferably a sodium or potassium salt of acetic or propionic acid, at a temperature below $30°$ C., preferably between about $-15°$ C. and about $10°$ C. and advantageously under conditions of agitation for several hours, eg. 2 to 50 hours, to form the corresponding dodecyl isomeric mixture of 2-(2'-nitrophenylazo)-4-dodecyl-phenols obtained as an oily liquid phase over an aqueous phase containing water, acid and salts. The oily phase is separated by decantation or by any other convenient method, and can be Accordingly, the crude liquid mixture containing the triazole mixture obtained above is purified by treatment at a temperature in the range of from $20°$ C. to about $150°$ C. with between about 5 and about 30 mole percent, preferably 10 to 20 mole percent, of an organic anhydride selected from the group consisting of alkyl anhydrides containing from 3 to 8 carbon atoms, such as propionic anhydride, acetic anhydride, acetic formic anhydride and aromatic anhydrides of 8 to 12 carbon atoms such as phthalic anhydride and succinic anhydride. The preferred anhydrides, however, are acetic and propionic anhydride. This treatment with the organic anhydride is usually conducted over a period of from about 0.5 to 5 hours and is effected preferably at a temperature between about $30°$ C. and about $100°$ C. at atmospheric or slightly superatmospheric pressure. The anhydride converts undesirable color forming impurities, for example, aminophenol by-products which impart a black or dark brown coloration to non-distillable amides so that, in the subsequent distillation conducted under vacuum, these impurities remain in the distilland and are not recovered overhead in the $180°$ to $250°$ C. boiling distillate fraction containing product. The anhydride treated mixture is then vacuum distilled, eg. under a pressure of between 0.01 mm and 0.15mm Hg, preferably between 0.02 and 0.06 mm Hg.

The disillate fraction is preferably further treated by contact with air, oxygen or oxygen enriched air, for example, an air and ozone mixture, most preferably for a period of from 0.5 to 25 hours, at a temperature between about $50°$ C. and about $150°$ C., most desirably between about 70° C. and about 120° C., to convert any remaining color forming impurities, for example, phenolguinone by-products which impart a yellow coloration and any remaining aminophenols to non-distillable polymers or other Accordingly, the crude liquid mixture containing the triazole mixture obtained above is purified by treatment at a temperature in the range of from 20° C. to about 150° C. with between about 5 and about 30 mole percent, preferably 10 to 20 mole percent, of an organic anhydride selected from the group consisting of alkyl anhydrides containing from 3 to 8 carbon atoms, such as propionic anhydride, acetic anhydride, acetic formic anhydride and aromatic anhydrides of 8 to 12 carbon atoms such as phthalic anhydride and succinic anhydride. The preferred anhydrides, however, are acetic and propionic anhydride. This treatment with the organic anhydride is usually conducted over a period of from about 0.5 to 5 hours and is effected preferably at a temperature between about 30° C. and about 100° C. at atmospheric or slightly superatmospheric pressure. The anhydride converts undesirable color forming impurities, for example, aminophenol by-products which impart a black or dark brown coloration to non-distillable amides so that, in the subsequent distillation conducted under vacuum, these impurities remain in the distilland and are not recovered overhead in the 180° to 250° C. boiling distillate fraction containing product. The anhydride treated mixture is then vacuum distilled, eg. under a pressure of between 0.01 mm and 0.15mm Hg, preferably between 0.02 and 0.06 mm Hg.

The distillate fraction is preferably further treated by contact with air, oxygen or oxygen enriched air, for example, an air and ozone mixture, most preferably for a period of from 0.5 to 25 hours, at a temperature between about 50° C. and about 150° C., most desirably between about 70° C. and about 120° C., to convert any remaining color forming impurities, for example, phenolquinone by-products which impart a yellow coloration and any remaining aminophenols to non-distillable polymers or other and periods of retention. Also, the substantially long branched chain dodecyl substituents provide better compatibility with high molecular weight hydrocarbon polymers and non-polymeric materials, and the composition comprising a mixture of the dodecyl isomers has greater solubility in polyolefins than any of the individual components of the mixture or the n-dodecyl isomer alone.

The substantially increased solubility of the present isomeric mixture over the individual solubilities of the individual components is indeed unexpected and may be explained by the interaction and association of the various isomeric components in the composition; these molecules are not sufficiently similar to allow for the formation of crystals and, hence, the present isomeric mixtures are not solids.

Surprisingly, applicant has also discovered that excessive branching, such as is present in the hexamethyl hexyl substituent, is undesirable when present in a major proportion in the isomeric mixture for the reason that the molecular shape or thickness of such dodecyl substituents seems to prevent easy entry into the intersticies of the polymeric material. As result, such excessively branched dodecyl hydroxyphenyl benzotriazoles are usually absorbed only on the surface of the polymer and are subject to exudation from the surface sites of the polymer and removal by surface abrasion in a relatively short period of time; eg. a few months.

The mixture of isomers in the composition of the present stabilizers is responsible for maintaining the liquid state and for providing a UV absorption range which peaks at between 280 nm and 340 nm and which is particularly effective over the range of 260 nm to 370 nm for maximum protection as a complete sun screen. The positioning of the dodecyl substituents para to the —OH group is also important in providing an unhindered phenol moiety which possesses a higher efficiency against heat deterioration. The present isomeric mixtures possess advantages over other alkyl hydroxyphenyl benzotriazoles which disclose efficiencies in the border areas of the 200 nm or 400 nm range and which are useful for only a limited number of polymers.

The polymeric materials stabilized by the present isomeric liquid mixtures include homopolymers and copolymers of hydrocarbon olefins such as ethylene, propylene, butylene and styrene, homopolymers and copolymers of olefin halides such as vinylchloride, vinylidine chloride, and 2,3,-dichloro-1,3-butadiene, and homopolymers and copolymers of esters such as vinyl acetate, methyl methacrylate, etc. and cellulose and carbonate polymers. Terpolymers of any of the above monomers are also suitable for stabilization with the present isomeric liquid mixture. The present stabilizers are utilized in a concentration within the range of between about 0.05 and 15 weight percent preferably between about 0.1 and about 10 weight percent, most preferably between about 0.5 and about 5 weight percent based on the polymer. The liquid mixture of isomers can be incorporated by spraying on a particulate or powdered dry polymer or by adding the stabilizer to a suspension of polymer in a low molecular weight alcohol or other dispersant.

They can also be most intimately incorporated in the polymer by adding the stabilizer to the reaction during the polymerization or before curing the polymer or by immersion of the polymer in a solution of the stabilizer after polymerization is complete followed by evaporation of stabilizer solvent. Frequently, such incorporations by immersion can be effected at room temperature which is greatly advantageous in the stabilization of certain dyes and other materials which do not possess high thermal stability.

These methods of incorporating the present stabilizers in the polymeric composition are generally carried out under conventional temperature and pressure conditions which are within the range of between about 130° C. and about 250° C. under atmospheric to 50 psig. pressure, preferably between about 175° C. and about 210° C. at atmospheric pressure. In certain circumstances, when the stabilizer is added to the polymerization reaction mixture or before compounding and curing the polymer, the temperature and pressure extant in the system may be employed. Actually, the operable limit of conditions for addition of stabilizer may be widely varied because of the normally liquid state of the present isomeric mixture. Thus, it is possible to employ temperatures between about −30° C. and 200° C. under atmospheric pressure and even higher temperatures under superatmospheric pressure, when desired.

The liquid isomeric mixture may additionally contain antioxidant, for example, a sterically hindered phenol such as 2,6-ditertiarybutyl-4-methylphenol (Ionol); dilaurylthio-propionate; dietertiarybutyl-4-nonylphenol (Uvinox-1494); etc. or any other useful antioxidant. Alternatively, the present liquid isomeric mixture can be incorporated into a final polymeric formulation including the antioxidant and other additives. When employed, between about 0.1 weight percent and about 5, weight percent, more usually 0.25 to 1.5 weight percent, of antioxidant based on oxidizable species has been found suitable.

The present stabilizers are highly effective for providing stability in olefinic polymers used in making transparent sheets or films employed as a sun screen or barrier against water evaporation; in vinyl halide polymers employed as sliding or roofing materials or as floor tile; in preventing yellowing of polystyrene sheets or molded forms used in lighting fixtures and in many other applications involving the use of butylene acetate, cellulose ester and acrylic polymers.

The present stabilizers may also be employed to prevent deterioration due to discoloration and oxidation in non-polymeric materials used as commercial dyes including azo or azoic dyes, anthraquinone dyes, carbazole dyes, sulfur-containing dyes, indigoid dyes and their intermediates and ionized dye derivatives. These stabilizers provide similar protection in lacquers, paints and varnishes. Specifically "chalking" of body finishes in automobiles and other items subjected to constant exposure to the elements can be greatly reduced. Because of its high solubility in varnishes, for example, soybean alkyd varnishes, the present stabilizers can be incorporated in concentrations as high as 10% to 15% to provide an exceptionally resistant finish.

For cosmetic uses, the liquid isomeric mixture can be employed in the absence or presence of a non-irritating antioxidant such as Ionol. Suitable for stabilization with the present isomeric mixtures are cosmetic preparations including cosmetic creams to prevent color degradation and promote shelf life. Use in hair dyes, conditioners or hair sprays or cosmetic ointments is particularly attractive since the present stabilizers act as barriers to completely screen out the harmful effects of the sun. In such applications, stabilizer concentrations of from 0.01% up to 15%, preferably 1% to 10% may be used. These and many other applications of the present stabilizers will become apparent from consideration of the solubility characteristics of the present liquid isomeric mixtures.

Solvents suitable for the present stabilizers include low and high boiling water immiscible organic solvents and low boiling water soluble organic solvents and dispersants. Examples of these include lower alcohols example ethanol, methanol, propanol, etc., lacquer, vehicles; oils, for example, white petrolatum, paraffin oil, linseed oil, castor oil, oil of rose, mineral or vegetable oils, olive oil, glycerin, vaseline, cocoa butter, lanolin, light pertoleum oils or lubricating oils; aromatic solvents, for example benzene, toluene or xylene; higher alcohols; resorcinol; ketones; alkyl pyrrolidones, cycloaliphatic hydrocarbons for example cyclohexane; pyrogallic acid; fatty esters; water based emulsions alkoxy alkyl acetate; ethyl- and butyl-cellusols; ethylene glycol; terpentine; bisphenols; hydroxy biphenols; triphenyl phosphate and other organic phosphates; sterically hindered phenols; for example, Ionol; phthalates for example, benzylphthalate and dibutylphthalate, ethers, for example Cellosolve, Solox and many others.

The liquid state of the present liquid isomeric mixtures allows intimate dispersion throughout the material to be stabilized without the use of solvents. However, from the standpoint of economics and as a means of extending the distribution of stabilizers, a solvent or dispersant is most frequently employed. When used, the solvent or dispersant may comprise up to 80% by weight or more of the isomeric mixture.

Generally, the stabilizer is incorporated in the non-polymeric material in a manner similar to that outlined above except for obvious modifications in procedure. For example, in place of stabilizer addition to the polymer or polymerizing species, the stabilizer can be added to the carrier vehicle or may be added to a dye, dye intermediate or cosmetic formulation.

The following examples are offered in illustration and are not to be construed as limiting to the scope of the invention as set forth in the preceding discussion and as defined by the claims. All parts and proportions referred to herein and in the appended claims are in parts by weight unless otherwise indicated.

EXAMPLE I

Hydrochloric acid (200 ml., 31%) is added to a solution of 2-nitroaniline (100 gm., 0.8 mole) in glacial acetic acid (400 ml.). To the resulting slurry, cooled to $-5°$ C., is added 150 ml. of 38% (wt./vol.) sodium nitrite solution (0.84 L mole). After neutralization of the excess nitrite with 4.4 gms. of sulfamic acid, a mixture of branched 4-dodecylphenol isomers (209 gm. of mixture, 0.8 mole)* is added to the solution. Anhydrous sodium acetate (140 gm.) is then gradually added to the solution, the temperature of which is maintained at or below 10° C. The mixture is maintained at pH of about 4 and is stirred for 11 hours at 10° C., and then gradually allowed to warm to 25° C. After 31 hours the coupling is complete, and a 2-phase liquid is formed comprising an oily dye layer above an aqueous layer. The oily dye layer is separated from the aqueous layer and washed with water to give the corresponding mixture of branched dodecyl isomers of 2-(2-nitrophenylazo)-4-dodecylphenol.

*Mixture obtained from the polymerization of propylene to the tetramer at 70° C. in the presence of 1% $BF_3$ followed by reaction of the tetramer mixture with phenol at 60° C.

The oil layer consisting of the 2-(2-nitrophenylazo)-4-dodecyl-phenols is dissolved in benzene (140 ml) and methanol (560 ml.), cooled to 15° C. and treated with 135 ml. of 40% (wt./vol.) sodium hydroxide solution while the temperature is kept below 15° C. After the addition of 95.2 gm. of zinc dust (1.45 moles), the mixture refluxed for 8 hours. The benzene, methanol, and water are removed by distillation, and the remaining mixture is treated with 750 ml. of 31% hydrochloric acid. An aqueous and an organic layer are formed. The organic layer is separated from the aqueous layer and washed twice with water and the water-washed product is vacuum distilled to recover a fraction boiling at 197°–220° C. (at 0.15 mm Hg) which is a mixture of branched chain dodecyl, isomers of 2-(5'-dodecyl-2'-hydroxyphenyl) benzotriazole containing substantially no n-dodecyl isomer and a predominance of isomers having at least 7 carbon atoms in its alkyl backbone, which is the longest chain of carbon atoms attached to the benzene ring of the individual isomer.

EXAMPLE II

The product of Example I is further purified by contacting with 16 mls. of acetic anhydride at 70° C. for 120 minutes with stirring and then distilled at 170° C. to 270° C. under 0.03 mm Hg whereupon a distillate boiling between 140° C. and 220° C. is collected and condensed. The distillate is then blown with air at 95° C. for 20 hours after which it is again distilled under 0.03 mm Hg and a fraction boiling between 190° C. and 220° C. is collected and condensed as the second distillate fraction. This second distillate fraction is a normally liquid mixture of branched chain dodecyl isomers of 2-(5'-dodecyl-2'-hydroxyphenyl) benzotraizole which does not freeze at a temperature of −50° C. and contains substantially no n-dodecyl isomer and a predominance of branched dodecyl substitute containing at least 7 carbon atoms in the linear alkyl backbone.

EXAMPLE III

A recent patent, U.S. Pat. No. 3,230,194 proposes stabilization of polymeric materials against ultraviolet light deterioration by the use of 2-(2'-hydroxy-5'-tert-octylphenyl) benzotriazole. This patent reports that 2-(2'-hydroxy-5'-tert-octylphenyl) benzotriazole (0.1% by weight) is milled into low density polyethylene and 10-mil sheets are molded. The sheets are exposed outdoors for 80 days; carbonyl formation and percent ultimate elongation of this and other benzotriazole compounds are reported as follows:

TABLE

| | Percent C=O | Percent Ultimate Elongation |
|---|---|---|
| Unstabilized (control) | 0.259 | 70 |
| 2-(2-Hydroxy-5-methylphenyl)benzo triazole | 0.283 | 52 |
| 2-(2-Hydroxy-5-tert-octylphenyl) benzo triazole | 0.098 | 706 |
| 2-(2-Hydroxy-5-n-dodecylphenyl) benzo triazole | 0.197 | 432 |

By way of comparison, the 2-(5'-dodecyl-2'-hydroxyphenyl) benzotriazole isomeric mixture of the present invention are prepared in Example I (0.1% by weight) is molded into low-density polyethylene* sheets of 10 mil thickness and tested as above for percent carbonyl formation and percent ultimate elongation. After 200 Weatherometer hours (corresponding to about 80 day of outdoor exposure) the present mixture of branched chain dodecyl isomers of 2-(5'-dodecyl-2'-hydroxyphenyl) benzotriazole of Example I shows a percent ultimate elongation of more than 700% and a carbonyl formation substantially equal to the tertiary octyl hydroxy benzotriazole in the Table. Comparing these results with the results obtained in the above table, it is found that the present branched chain dodecyl isomers shown significant and distinct improvement in the ultimate elongation and carbonyl formation properties of the polyethylene polymer over the n-dodecyl isomer.
* having equivalent % carbonyl and % elongation as the control in the Table.

The above testing for % carbonyl development with patentees' 2-(5'-tert-octyl-2'-hydroxyphenyl) benzotriazole and with the present isomeric mixture of 2-(5'-dodecyl-2'-hydroxyphenyl) benzotriazole as prepared in Example I is repeated except that the respective samples are subjected to 238 Weatherometer hours and polypropylene with 0.1% by weight of the respective stabilizers is milled into 10 mil sheets. In this series of tests, the 2-(5'-tert-octyl-2'-hydroxyphenyl) benzotriazole shows slightly less carbonyl development than the control (unstabilized polyproylene) whereas the branched-chain 2-(5'-dodecyl-2'-hydroxy-phenyl) benzotriazole isomeric mixture shows about half as much carbonyl development as the control. U.S. Pat. No. 3,230,194 would lead one to except otherwise since it was reported that results obtained with polypropylene are similar to those reported for polyethylene. Accordingly, one might except the same high carbonyl development for the n-dodecyl derivative as was demonstrated in the case of polyethylene stabilization in the above table. Conversely, the present branched chain dodecyl isomeric mixture shows a reverse trend in reducing the carbonyl development by about half.

These good results, taken together with the liquid character state of the instant stabilizers, which permits uniform and intimate dispersion in the polymeric species, indicate the important advance which applicant has made in stabilization with benzotriazoles.

EXAMPLE IV

About 2% of an isomeric mixture of about equal portions of 2-(5'-methylisopropyl octyl-2'-hydroxyphenyl) benzotriazole 2-(5'-triethylhexyl-2'-hydroxyphenyl) benzotriazole, 2-(5'-di-methyldecyl-2'-hydroxyphenyl) benzotriazole, 2-(5'-pentamethyl-heptyl-2'-hydroxyphenyl) benzotriazole, 2-(5'-tetramethyloctyl-2'-hydroxyphenyl) benzotriazole, 2-(5'-methylethylmonyl-2'-hydroxy-phenyl) benzotriazole and 2-(5'-diethyloctyl-2'-hydroxyphenyl) benzotriazole is prepared by selectively mixing these components and the resulting mixture is incoporated in polyvinyl chloride plastic by melt incorporation at 350° C. in Brabender mixer. The pellets are formed into ⅛ inch thick sheet in a Carver press and then exposed for 600 hours to average daylight conditions. The results of this test show 0% discoloration, and no visible evidence of crazing or other signs of deterioration.

EXAMPLE V

Into a glass reactor equipped with an ice bath and stirrer and containing 140 grams (1 mole) of 2-nitroaniline in 200 ml of 31% HCl and 400 ml glacial acetic acid is added 275 grams (1.04 mols) of 38% sodium nitrite. The resulting solution of 2-nitrophenyl diazonium chloride is stirred at 0° C. to 5° C. for 1.5 hours and the excess sodium nitrite is neutralized with sulfamic acid.

A liquid mixture of branched chain dodecyl isomers of 4-dodecylphenol is obtained by reacting at 0° C. in the presence of boric-oxalic acid, phenol with a stoichometric amount of propylene tetramer obtained from the polymerization of propylene at 80° C. under/atmosphere pressure in the presence of Al:Ti catalyst and containing 6 isomers wherein at least 80% of the isomeric mixture contains the 2, 4, 6, 8-tetramethyloctyl and other isomers having at least 7 carbon atoms in the alkyl backbone.

About 372 grams (1.2 mols) of the liquid mixture of branched chain dodecyl isomers of 4-dodecylphenol is added to the above solution of 2-nitrophenyl diazonium chloride and stirred for about 20 hours at 5° C. in the glacial acetic acid medium which is maintained at a pH of 4.5.

To this mixture is then added 150 grams of sodium acetate at 5° C. and the mixture stirred for 31 hours at a pH of about 4.5 to form the corresponding dodecyl isomeric mixture of 2-(2'nitrophenylazo)-4-dodecylphenols as an oily liquid layer superimposed over an aqueous layer containing water, salt and mineral acid.

The oily layer is separated by decantation, diluted with 200 ml benzene and 500 ml methanol, cooled to 15° C. and the 2-(2'-nitrophenylazo)-4-dodecylphenols cyclized to 2-(5'-dodecyl-2'-hydroxyphenyl) benzotriazoles by refluxing for about 6 hours in the presence of 92.2 grams zinc dust in 500 ml of 40% (wt./vol.) aqueous sodium hydroxide solution.

After recovery, the corresponding normally liquid mixture of branched chain dodecyl isomers of 2-(5'-dodecyl-2'-hydroxy-phenyl)benzotriazole, is then intimately mixed with 16 to 20 gms of acetic anhydride at 90° C. for 3 hours to convert color forming impurities to high boiling non-distillable materials and the resulting solution is distilled under 0.02 mm Hg pressure to separate a distillate fraction boiling between 180° C. and 250° C. The distillate fraction is collected, condensed and blown with air for 16 hours at 100° C. to convert any remaining color-forming impurities to high-boiling non-distillable materials and the air treated distillate fraction is then re-distilled under reduced pressure to separate a distillate fraction boiling between 185° C. and 220° C. which is the substantially pure 2-(5'-dodecyl-2'-hydroxyphenyl) benzotriazole isomer mixture containing substantially no color-forming inpurities and wherein the dodecyl isomers of the isomeric mixture correspond to the dodecyl tetramer used in the above preparation of the isomeric 4-dodecylphenol.

EXAMPLE VI

A mixture of nonyl substituted benzotriazoles were prepared in a manner similar to that of Example V by substituting nonylphenol prepared by reacting with propylene trimer instead of tetramer as in Ex. 5. The final product was distilled at 0.4 mm Hg and gave a fraction having a b.p. 180°–200° C., a $K_{max}$ of 42.1 at 335 nm. A sample of this material was incorporated in polypropylene as was Uvinul ® 410. ⅛% of the product of this example provided greater protection against embrittlement from 300 hours of Fadometer ® exposure than ¼% of Uvinul 410.

EXAMPLE VII

The following formulations are milled for 10 minutes at 350° C. in a Brabender mixer

| Components | Sample I (% by weight) | Sample II (% by weight) |
|---|---|---|
| polypropylene | 99.6 | 99.6 |
| isomeric triazole product mixture of Example V | 0.125 | 0 |
| (2,6-ditert-butyl-4-ethyl) phenol (Ionol) | .25 | .25 |
| 2-(5'-tert-octyl-2'-hydroxyphenyl) benzotriazole | 0 | 0.125 |

The above blended materials of Samples 1 and 2 are separately pressed into sheets of 25 ml thickeners on a Carver press at 350° C. The sheets of Samples 1 and 2, after cooling, are cut into 2 × 0.5 inch strips and separately subjected to 600 hours exposure on the Weatherometer ®. After 600 hours exposure, the strips of Sample 1 are compared with the strips of Sample 2. The strips of Sample 2 show pronounced crazing and slight yellowing; whereas the strips of Sample 1 show slight crazing and no discoloration whatever.

EXAMPLE VIII

A sample (1) of polypropylene fabric dyed with 0.5% its weight of Nyliton Scarlet DYL is immersed for 45 minutes in a bath containing the isomeric mixture of triazole stabilizers of Example II amounting to 0.5% weight of the fabric sample in 10 ml of dimethylformamide.

A similar sample (2) of polypropylene is immersed in a similar bath containing the same amount of 2-(5'-tertoctyl-2'-hydroxyphenyl) benzotriazole. Both baths are maintained at 90° C. After 45 minutes the fabric samples are removed, rinsed with water and dried. The dryed samples are then separately subjected to 10 hours on the Fadeometer ®. Sample 2 shows noticeable signs of fading whereas Sample 1 shows no weakening of color.

EXAMPLE IX

A formulation of 99.6% by weight Ba-Cd rigid polyvinyl chloride, 0.25% by weight Ionol and 0.125% by weight of the isomeric triazole product mixture of Example II is milled for 10 minutes at 350° C. in a Brabender mixer to provide Sample A. A Sample B is prepared by repeating this procedure except that the triazole isomeric mixture is omitted and 99.75% by weight of the polyvinyl chloride is employed.

Each of the above milled samples are pressed into 25 mil sheets at 350° C. on a Carver press and 2 × 0.5 inch strips are cut from each sample. These strips are then subjected to 900 hours of exposure in the Weatherometer ®. After exposure Sample A shows no discoloration whatever; whereas Sample B is distinctly yellow.

EXAMPLE X

A formulation of 99.6% by weight of polystyrene (30% in toluene), 0.125% by weight Ionol and 0.25% by weight of the isomeric triazole product mixture of Example II is cast into a thin film with a Bird film applicator. This procedure is repeated with the formulation of 99.87% by weight polystyrene and 0.125% Ionol and the first and second formulation films compared after being exposed to 600 hours on the Weatherometer ®. The film of the first formulation shows no yellowing whereas the film of the second formulation is distinctly yellowed.

EXAMPLE XI

The following paste formulations for sun screens are prepared

| Components | Formula I 3% paste | Formula II 2% paste |
|---|---|---|
| isomeric triazole product mixture of Example V | 1 oz. | 1 oz. |
| Polyoxyethylated vegetable oil | 32 oz. | — |
| isopropyl stearate | — | 34 oz. |
| polyoxyethylated sorbitan monopalmitate | — | 15 oz. |

The above paste formulations are separately mixed to give a clear solution and each solution separately applied to the skin in small portions on the arm of the test subject. After about one hour exposure to the sun, the untreated portions of the skin show reddening and signs to burn, whereas both of the treated portions develop tan without signs of burning.

EXAMPLE XII

The present isomeric mixture of triazoles is also tested for gloss retention and light fastness in paints and varnish by preparing the following samples.

| Components | Sample A (wt. %) | Sample B (wt. %) |
|---|---|---|
| Soya Bean-alkyd paint (beige color) | 99 | — |
| Spar varnish | — | 99 |
| Isomeric triazole product | | |

-continued

| Components | Sample A (wt. %) | Sample B (wt. %) |
| --- | --- | --- |
| mixture of Example II | 1 | 1 |

The above mixtures are individually stirred until homogeneous and the samples individually applied to a clay-coated paper with a Bird Film Applicator and dried at 70° C. Exposure of Sample A in a Fadeometer for 100 hours shows the film has significantly improved gloss retention and light fastness over a control film similarly prepared but without incorporation of the present stabilizer.

Exposure of Sample B in a Fadeometer® for 100 hours shows the film has significantly improved gloss retention over a control film similarly prepared but without incorporation of the present stabilizer.

In both of the above samples containing stabilizer, no fading of color is visible after 25 hours exposure in the Fadeometer.

EXAMPLE XIII

A first formulation of a furniture polish is provided by forming a melt on a steam bath of 9 oz. carnauba wax, 1.5 pints turpentine and 1.75 pints of hot water containing 2 ox. of soap.

A second formulation of a furniture polish is also provided by repeating the first formulation and adding thereto 2% by weight of the isomeric triazole product mixture of Example II, (based on Carnauba wax).

Both formulations are separately emulsified in a Waring blender and the resulting emulsions separately applied to stained, varnished oak. The first formulation, without the present triazole stabilizing mixture, yellows within one month; whereas the second formulation shows no signs of yellowing over the same period of time.

What is claimed is:

1. A normally liquid composition for stabilizing heat and light sensitive materials consisting essentially of branched-chain isomers of hydroxyphenyl benzotriazoles selected from the group consisting of a branched chain dodecyl isomeric mixture of 2-(5'-dodecyl-2'-hydroxyphenyl) benzotriazoles and a branched chain nonyl isomeric mixture of 2-(5'-nonyl-2'-hyroxyphenyl) benzotriazoles.

2. The composition of claim 1 wherein the branched chain isomeric mixtures are substantially free of their respective straight chain isomers.

3. A process for the preparation of the composition of claim 2 which comprises:
    (a) Coupling a 2-nitrophenyl diazonium salt with a normally liquid mixture of branched chain isomers of phenol selected from the group consisting of the branched chain nonyl isomers of 4-nonyl phenol and the branched chain dodecyl isomers of 4-dodecyl phenol in the presence of glacial acetic acid at a pH from about 3 to about 5.5 to form an oily liquid; and
    (b) Cyclizing the 2-(2' nitrophenylazo)-4-nonyl phenols and 2-(2' nitrophenylazo)-4-dodecyl phenols respectively formed to the corresponding triazoles in a solution with a zinc catalyst in the presence of an aqueous inorganic hydroxide which forms the corresponding normally liquid mixture of claim 2.

4. The process of claim 3 wherein the product of step b) is further contacted with from about 5 to about 30 mole percent of an organic anhydride selected from the group of alkyl anhydride having from 4 to 8 carbon atoms, phthalic anhydride and succinic anhydride and distilling the resulting liquid under vacuum, 0.01 to 0.15 mm Hg pressure, to separate a distillate fraction boiling between about 180° C. and about 250° C. and recovering the corresponding normally liquid mixture of branched chain isomers selected from the group consisting of 2-(5'-nonyl-2'-hydroxyphenyl) benzotraizole and 2-(5'-dodecyl-2'-hydroxyphenyl) benzotriazole.

5. The process of claim 4 wherein the organic anhydride is acetic anhydride.

6. The process of claim 4 wherein the normally liquid distilled mixture is contacted with oxygen and redistilled under 0.02 mm to 0.06 mm Hg pressure to separate a distillate fraction boiling between about 180° C. and about 230° C. and recovering the correspondingly normally liquid mixture of branched chain isomers selected from the group consisting of 2-(5'-nonyl-2'-hydroxyphenyl) benzotriazole and 2-(5'-dodecyl-2'-hydroxyphenyl) benzotriazole.

7. The process of claim 6 wherein the normally liquid distilled mixture is contacted with air at a temperature between about 50° C. and about 150° C.

8. The composition of claim 1 wherein the branched chain isomeric mixture is a branched chain nonyl isomeric mixture of 2-(5'-nonyl-2'-hydroxyphenyl)benzotriazoles.